(12) United States Patent
Biscup

(10) Patent No.: US 6,786,930 B2
(45) Date of Patent: Sep. 7, 2004

(54) MOLDED SURGICAL IMPLANT AND METHOD

(75) Inventor: Robert S. Biscup, Chagrin Falls, OH (US)

(73) Assignee: Spineco, Inc., Avon, OH (US)

( * ) Notice: Subject to any disclaimer, the term of this patent is extended or adjusted under 35 U.S.C. 154(b) by 169 days.

(21) Appl. No.: 09/971,395

(22) Filed: Oct. 5, 2001

(65) Prior Publication Data

US 2004/0117015 A1 Jun. 17, 2004

Related U.S. Application Data

(60) Provisional application No. 60/286,073, filed on Apr. 24, 2001, and provisional application No. 60/250,831, filed on Dec. 4, 2000.

(51) Int. Cl.$^7$ .............................................. A61F 2/28
(52) U.S. Cl. ..................................... 623/16.11; 623/901
(58) Field of Search .............................. 623/901, 11.11, 623/16.11; 128/898; 433/223

(56) References Cited

U.S. PATENT DOCUMENTS

| | | | |
|---|---|---|---|
| 4,373,217 A | | 2/1983 | Draenert |
| 4,575,805 A | * | 3/1986 | Moermann et al. ......... 700/163 |
| 4,843,112 A | | 6/1989 | Gerhart et al. |
| 4,849,285 A | | 7/1989 | Dillon |
| 4,936,862 A | * | 6/1990 | Walker et al. .............. 128/898 |
| 5,027,281 A | * | 6/1991 | Rekow et al. .............. 700/182 |
| 5,150,304 A | * | 9/1992 | Berchem et al. ............ 700/182 |
| 5,443,510 A | * | 8/1995 | Shetty et al. .................. 419/2 |
| 5,555,884 A | * | 9/1996 | Nonomura .................. 600/420 |
| 5,768,134 A | * | 6/1998 | Swaelens et al. ........... 700/121 |
| 6,112,109 A | * | 8/2000 | D'Urso ....................... 600/407 |
| 6,224,629 B1 | | 5/2001 | Lin et al. |
| 6,245,108 B1 | | 6/2001 | Biscup |
| 6,254,639 B1 | * | 7/2001 | Peckitt .................... 623/11.11 |
| 6,261,583 B1 | | 7/2001 | Dunn et al. |
| 6,277,151 B1 | | 8/2001 | Lee et al. |
| 6,463,351 B1 | * | 10/2002 | Clynch ....................... 700/163 |
| 2002/0007294 A1 | * | 1/2002 | Bradbury et al. .............. 705/7 |

OTHER PUBLICATIONS

United States Provisional Ser. No. 60/286,073, filed Apr. 24, 2001, entitled "Mold–Injected Surgical Implant".

* cited by examiner

*Primary Examiner*—Eduardo C. Robert
(74) *Attorney, Agent, or Firm*—Fay, Sharpe, Fagan, Minnich & McKee (57) ABSTRACT

A customized prosthetic implant and method for producing a customized prosthetic implant for use in fully or partially replacing bone and/or tissue in a human or animal. The custom prosthetic implant is produced by obtaining information about the site of implant for the prosthetic implant, processing the obtained information to generate information on the size and shape of the prosthetic implant, and transferring at least a portion of the generated information to a molding machine to at least partially form the custom prosthetic implant from a moldable compound.

29 Claims, 4 Drawing Sheets

MOLDED SURGICAL IMPLANT AND METHOD

This patent application claims priority on U.S. Provisional Application Serial No. 60/250,831, filed Dec. 4, 2000, entitled "Mold-Injected Spinal Fusion Cage," and U.S. Provisional Application Serial No. 60/286,073, filed Apr. 24, 2001, entitled "Mold-Injected Surgical Implant."

The present invention pertains to prosthetic implants, and more particularly to interbody prosthetic implants to replace one or more bones and/or cartilaginous bodies, and/or to fuse together two or more bones, and even more particularly to interbody spinal prosthetic implants that provide a substitute for an intervertebral disc and/or that provide a flexible spacer between two vertebrae.

INCORPORATION BY REFERENCE

U.S. Provisional Application Serial No. 60/250,831, filed Dec. 4, 2000, entitled "Mold-Injected Spinal Fusion Cage" and U.S. Provisional Application Serial No. 60/286,073, filed Apr. 24, 2001, entitled "Mold-Injected Surgical Implant" are incorporated herein by reference. Also incorporated herein by reference is U.S. Pat. No. 6,245,108, issued Jun. 12, 2001 entitled "Spinal Fusion Implant" which illustrates one of many types of prosthetic implants that can be implanted in an intervertebral disc space.

BACKGROUND OF THE INVENTION

The human spine is made up of a column of thirty-three bones and their adjoining structures. The vertebrae near the head are known as the presacral vertebrae, which are separate bones capable of individual movement. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs form a central axis that supports the head and torso. These vertebrae also enclose an opening through which the spinal cord passes there between.

The presacral vertebrae are normally held in position to one another by the intervertebral discs, ligaments and musculature of the body. These vertebrae move relative to adjacent vertebrae thus permitting the head to be turned relative the body and providing a wide range of flexibility to the spine.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compressing the neural structures causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniation of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine, due to the relatively large number of vertebrae, the minor loss of mobility is typically acceptable.

During a spinal fusion following a discectomy, a prosthetic implant or spinal implant is inserted into the intervertebral space. This prosthetic implant is often a bone graft removed from another portion of the patient's body, termed an autograph. The use of bone taken from the patient's body has the important advantage of avoiding rejection of the implant, but has several shortcomings. There is always a risk in opening a second surgical site in obtaining the implant, which can lead to infection or pain for the patient, and the site of the implant is weakened by the removal of bony material. The bone implant may not be perfectly shaped and placed, leading to slippage or absorption of the implant or failure of the implant to fuse with the vertebrae.

Other options for a graft source of the implant are bone removed from cadavers, termed allograft, or from other species, termed a xenograft. In these cases, while there is the benefit of not having a second surgical site as a possible source of infection or pain, there is increased difficulty of the graft rejection and the risk of transmitting communicable diseases.

An alternative approach is using a bone graft or using a manufactured implant made of a synthetic material that is biologically compatible with the body and the vertebrae. Several compositions and geometries of such implants have been utilized, ranging from simple blocks of material to carefully shaped implants, with varying success.

There have been an extensive number of attempts in developing an acceptable prosthetic implant that can be used to replace an intervertebral disc and yet maintain the stability of the intervertebral disc spaced between adjacent vertebrae, at least until complete arthrodesis is achieved. These prosthetic implants have taken many forms. While many types of synthetic prosthetic implants have been proposed, the success ratio has been low and the surgical procedures have been complicated and often traumatic to the patient.

One of the more prevailing designs of these prosthetic implants takes the form of a cylindrical implant. Brantigan U.S. Pat. No. 4,878,915 and Ray U.S. Pat. No. 4,961,740 represent these types of prosthetic implants. In these cylindrical implants, the exterior portion of the cylinder can be threaded to facilitate insertion of the prosthetic implant. Some of these prosthetic implants are designed to be pounded into the intervertebral disc space and the vertebral end plates. These types of devices are represented in Brantigan U.S. Pat. No. 4,834,757 and Brantigan U.S. Pat. No. 5,192,327. The Brantigan and Ray patents all disclose prosthetic implants wherein the transverse cross-section of the implant is constant throughout the length of the implant and is typically in the form of a right circular cylinder.

Other prosthetic implants have been developed that do not have a constant cross-section. For instance, the patent to McKinna U.S. Pat. No. 4,714,469 shows a hemispherical implant with elongated protuberances that project into the vertebral end plate. The implant of Bagby U.S. Pat. No. 4,934,848 is in the form of a sphere, which is positioned between the centrums of the adjacent vertebrae.

The various prosthetic implants can be generally divided into two basic categories, namely solid implants and implants designed to encourage bone ingrowth. Solid implants are represented by U.S. Pat. Nos. 4,878,915 and 4,349,921. The remaining patents discussed above include some aspect that permits bone to grow across the implant. It has been found that devices, which promote natural bone ingrowth, achieve a more rapid and stable arthrodesis. These implants are typically filled with autologous bone prior to insertion into the intervertebral disc space. These implants typically include apertures, which communicate with openings in the implant, thereby providing a path for tissue growth between the vertebral end plate and the bone or bone substitute within the implant. In preparing the intervertebral disc space for a prosthetic implant, the end plates of the vertebrae are preferably reduced to bleeding bone to facilitate tissue growth within the implant.

A number of difficulties remain with the many spinal implants currently available. While it is recognized that hollow implants which permit bone ingrowth in the bone or bone substitute within the implant are an optimum technique for achieving fusion, most of these devices have difficulty achieving this fusion, at least without the aid of some additional stabilizing device, such as a rod or plate. Moreover, some of these devices are not structurally strong enough to support the heavy loads applied at the most frequently fused vertebral levels, mainly those in the lower lumbar spine. Many of these problems have been overcome with the development of a novel prosthetic implant disclosed in U.S. Pat. No. 6,245,108. The design of the prosthetic implant in U.S. Pat. No. 6,245,108 optimizes the bone ingrowth capabilities between the prosthetic implant and the surrounding bone tissue and is strong enough to support the vertebrae until arthrodesis occurs, and maintains or restores the normal spinal anatomy at the instrumented segment. The novel prosthetic implant also exhibits reduced slippage when inserted between vertebrae and diminishes the occurrence of nerve pinching. Although prosthetic implant design has undergone substantial improvement, there still remains a need to quickly, accurately and cost effectively customize the size of the prosthetic implant for a particular patient.

In addition to vertebral injuries, prosthetic implants are used in many other areas of the body such as the hip, legs, arms, feet, hands, ribs and the like. Typically bones, segments of bones, and/or tissue about the bones and/or bone segments in one or more of these areas are replaced or repaired due to injury or damage to the bone and/or due to a genetic abnormality of the bone. In many instances, the bone or bone segment is replaced by metal pins, screws and/or rods. Although these bone replacements provide some anatomical substitute for the damaged and/or deformed bone, these bone replacements typically do not provide full function or range of movement that is provided by a healthy, properly formed bone. As a result, there is a need for a prosthetic implant that closely matches a bone and/or tissue to be replaced and which prosthetic implant can be quickly, accurately and cost effectively customizes to size for a particular patient.

SUMMARY OF THE INVENTION

The present invention pertains to prosthetic implants, and more particularly to interbody prosthetic implants to replace one or more bones and/or fibrocartilagous bodies, to fuse together two or more bones and/or fibrocartilagous bodies, and/or to replace tissue about bones and/or fibrocartilagous bodies, and even more particularly to interbody spinal prosthetic implants that provide a substitute for an intervertebral disc and/or that provide a flexible spacer between two vertebrae. The present invention also pertains to a method for forming the prosthetic implant. Although the present invention will be described with particular reference to interbody spinal prosthetic implants and a method for making the prosthetic implant and a method for inserting the prosthetic implant between one or more vertebrae, the invention has much broader applications and pertains to the formation of any type of bone for use in human or animal and a method for making such prosthetic implant and a method for inserting such prosthetic implant in the human or animal.

In accordance with the principal feature of the present invention, there is provided a prosthetic implant that is formed of a biologically compatible material for use in humans and/or animals. The prosthetic implant is shaped and sized to repair or be substituted for damaged bone, damaged cartilage and/or other types of tissue, malformed bone, and/or for insertion between two or more bones such as, but not limited to, two or more vertebrae. The shape of the prosthetic implant can include, but is not limited to, cylindrical shapes, spherical shapes, cubic shapes, cone shapes, pyramid shapes, prism shapes, and the like. In one embodiment, the prosthetic implant is designed to be placed in the intervertebral disc space that was formerly occupied by at least a portion of an intervertebral disc. The intervertebral disc is partially or completely removed prior to insertion of the prosthetic implant between two or more vertebrae. In another embodiment, the prosthetic implant is designed to replace one or more vertebra that has been damaged or that is malformed. In another embodiment, the prosthetic implant is designed to replace bones other than vertebrae that have been damaged or malformed. Such bones include, but are not limited to, acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, and/or zygomatic bone. In still another embodiment, the prosthetic implant is designed to be readily inserted by established surgical procedures, with minimal chances of surgical difficulty. In yet another embodiment, the geometry and materials of the prosthetic implant are selected to ensure proper load bearing, and desired load bearing and support. For instance, when the prosthetic implant is to be placed in the intervertebral disc space and/or substituted for a vertebra, the prosthetic implant is designed to ensure proper load bearing, desired load bearing and support through the vertebrae so as to reduce or minimize the likelihood of the prosthetic implant dislocating relative to the vertebrae during or after surgery. In still another embodiment, the shape and size of the prosthetic implant are selected to have an anatomically correct shape. For example, when the prosthetic implant is to be inserted between two vertebrae, the prosthetic implant is shaped to increase the area of contact with the vertebrae and/or to closely emulate the region formerly occupied by the intervertebral disk. In one aspect of this embodiment, the prosthetic implant, when placed in the intervertebral disc space, is designed such that the dimensions of the prosthetic implant are such that the two adjacently positioned vertebrae are caused to at least partially separate from one another a distance greater than their relative positions prior to surgery. The spreading of the adjacently positioned vertebrae from their original positions results in the elastic nature of the surrounding tissue and muscles maintaining the inserted prosthetic implant in compression between the vertebrae. In another aspect of this embodiment, the dimensions of the prosthetic implant are selected to cause two adjacently positioned vertebras to at least partially separate from one another a distance generally equal to or less than their relative positions prior to surgery. In still another aspect of this embodiment, the prosthetic implant is designed to reduce or eliminate nerve pressure caused by a damaged or removed intervertebral disc. In a still another embodiment, the prosthetic implant is capable of achieving arthrodesis (fusion) and/or arthroplasty (joint formation) between adjacent bones, depending on the desired procedure. As such, the prosthetic implant allows the surgeon to cause either a multidirectional joint or a fusion to form between two of more bones or on a portion of one bone.

In accordance with another aspect of the present invention, the prosthetic implant is made of a material that is inert or biologically compatible with a human or animal. The material can be partially bioabsorable, fully bioabsorable or non-bioabsorable. In one embodiment, the material is wear resistant. In still another embodiment, the material has an increased frictional coefficient. In another embodiment, the material has a reduced frictional coefficient. In yet another embodiment, the prosthetic implant is designed to maintain a tension load of about ten to forty pounds, and more preferably about fifteen to thirty-five pounds on the disc tissue and/or vertebral endplate when the prosthetic implant is implanted in an intervertebral disk space. This tension load facilitates in maintaining the prosthetic implant in position between the vertebrae and accelerates bone ingrowth between the vertebrae, if such bone growth is desired. As can be appreciated, other tension loads may be more appropriated for prosthetic implants used in different parts of a human or animal. In a further embodiment, the prosthetic implant is made of a material which closely approximates the elasticity of the bone and/or tissue being fully or partially replaced by the prosthetic implant. In another embodiment, the prosthetic implant is coated with, made up of, and/or contains a material which is radiolucent to enhance the visibility of the implant when exposed to X-rays, ultraviolet light, inferred light, etc. In a further embodiment, the prosthetic implant is coated with, made up of, and/or contains a material to enhance the visibility of the implant when exposed to sound waves, light waves, magnetic waves, and/or various types of electromagnetic waves.

In accordance with another aspect of the present invention, there is provided a prosthetic implant which includes a cage or a solid block design having a top wall, a bottom wall, a first end wall, a second end wall, a front side wall, and a back side wall. Such cage or solid block designs are typically placed in the intervertebral disk space that was formerly occupied by or adjacent to an intervertebral disk; however, the cage or solid block design can be used in other regions of the body of a human or other animal. In one embodiment, the front side wall and/or back wall of the cage extends substantially along the longitudinal axis of the cage and wherein the two side walls are configured to enhance the stability of the cage within the region the cage is to be inserted such as, but not limited to an intervertebral disk space. In one aspect of this embodiment, the front and/or back side wall is substantially planar. In another aspect of this embodiment, the front and/or back side wall is at least partially arcuate. In still another aspect of this embodiment, the front and back side wall have different face configurations. Cages that have configurations which include an arcuate front side wall surface and a substantially flat or planar back side wall, and are to be positioned in the intervertebral disk space, are typically positioned in the intervertebral disk space such that the substantially flat or planar surface of the back side wall is positioned closely adjacent to the spinal cord and the front side wall is positioned adjacent the peripheral edge of the intervertebral disk space. In yet another embodiment, the top wall and/or bottom wall are at least partially inclined along the longitudinal axis of the cage. The inclination of the top and/or bottom wall of the cage facilitates in the ease of insertion of the cage when the cage is to be inserted into the vertebrae column and/or provides a better fit for the cage within the intervertebral disk space since the inclination better matches the anatomical shape of the space between the vertebrae of the spinal column. In still yet another embodiment, the top wall and/or bottom wall are at least partially inclined between the front and back side walls of the cage. The inclination of the top and/or bottom wall of the cage facilitates in the ease of insertion into the vertebrae column and/or provides a better fit for the cage within the intervertebral disk space since the inclination better matches the anatomical shape of the space between the vertebrae of the spinal column. In still yet another embodiment, the cage of the prosthetic implant includes a top wall and/or bottom wall having at least one rigid surface adapted to engage the underside surface of adjacently positioned bone such as, but not limited to a vertebra within the intervertebral disk space. The ridge is designed to secure or bite into the bone surface. In one aspect of this embodiment, the top wall includes a plurality of ridged surfaces. In another aspect of this embodiment, the bottom wall includes a plurality of ridged surfaces. The ridged surfaces on the top and/or bottom wall can have a number of configurations. In another specific design, the ridge is a uniform structure extending over the lateral and/or longitudinal surface of the top and/or bottom wall. In still another aspect of this embodiment, the ridges are positioned on the top end and/or bottom wall and are spaced from the outer peripheral edge of the bottom and/or top wall. In still yet another aspect of this embodiment, the top and bottom wall have similar ridge configurations and a similar number of ridges; however, it can be appreciated that the top and bottom wall can have different numbers and/or different configurations of ridges. In a further aspect of this embodiment, the ridges in the top and/or bottom wall of the cage anchor the cage in between the bone and provide channels for bone ingrowth, which facilitates in the fusion of the bone. In a further embodiment, at least one or more edges of the cage are rounded off so as not to be sharp. The rounding off of the edges reduces and/or eliminates irritation about the prosthetic implant such as, but not limited to, pinching of the nerve leading from the spinal cord, which can result in pain, damage or paralysis to the individual. The rounded edges avoid or minimize nerve pressure that can be exerted on the nerves such as, but not limited to, nerves intervertebrally exiting the spinal cord. The one or more rounded off edges also facilitates with the insertion of the cage within the desired portion of the body such as, but not limited to, an intervertebral disk space. Examples of cage designs that encompass one or more of the embodiments discussed above are described and/or illustrated in U.S. Pat. No. 6,245,108, which is incorporated herein by reference.

In accordance with still another aspect of the present invention, at least a portion of the prosthetic implant has a generally spherical or ellipsoidal body. In one embodiment, the prosthetic implant has a generally spherical or ellipsoidal body. Such a generally spherical or ellipsoidal body of the prosthetic implant is typically placed in the intervertebral disk space that was formerly occupied by an intervertebral disk; however, the prosthetic implant can be designed for use in other regions of the body of a human or animal. In another embodiment, the prosthetic implant includes at least one stabilizer positioned at least partially about the outer surface of the generally spherical or ellipsoidal body of the prosthetic implant. The stabilizer is designed to facilitate in at least partially orienting the prosthetic implant between one or more bones, limiting the amount of movement of the generally spherical or ellipsoidal body between one or more bones, and/or facilitating in the insertion of the prosthetic implant between one or more bones. In one another aspect of this embodiment, the stabilizer is substantially disc shaped; however, the shape of the stabilizer is in no way limited to such a shape. In yet another aspect of this embodiment, the stabilizer includes one or more tapered edges. In still another aspect of this embodiment, the stabilizer is at least partially made of a porous material, a non-porous material, a non-biodegradable material, and/or a biodegradable material. In still yet another aspect of this embodiment, the stabilizer is coated with, contains and/or is made of a substance that promotes bone and/or other tissue growth, inhibits rejection of the prosthetic implant, reduces infection, reduces inflammation, reduces pain, promotes healing of surrounding tissue, performs a curative function (e.g., cancer medication, infection medication, etc.), functions as a location and/or visual indicator, and/or the like. In still yet another aspect of this embodiment, the stabilizer includes structural compounds (e.g., metals, ceramics, polymers, resins, fibers, etc.) to enhance the strength and/or rigidity of the stabilizer. In still another embodiment, the material at least partially forming the prosthetic implant is wear resistant. In a further embodiment, the material that at least partially forms the prosthetic implant increases or reduces the frictional coefficient of the prosthetic implant. In still a further embodiment, at least a portion of the surface of the prosthetic implant has and/or is coated to form smooth surfaces, rough surfaces, low frictional surfaces, wear resistant surfaces, and/or the like. In another embodiment, the prosthetic implant includes one or more openings and/or cavities. The openings and/or cavities can include various types of substances such as, but not limited to, medicine, tissue, cells, promoters, inhibitors, and/or visual and/or location indicators. In still another embodiment, the prosthetic implant includes a coating with one or more substances that migrate from the coated material into the surrounding tissue.

In accordance with still yet another aspect of the present invention, the prosthetic implant has a substantially smooth outer surface or includes regions having a substantially smooth outer surface to prevent or substantially prevent bone growth and/or other tissue growth on the substantially smooth surface and/or into the interior of the prosthetic implant. The substantially smooth surface allows for free or relatively free movement between tissue and/or one or more bones. The growth of bone or tissue into and/or on the surface of the prosthetic implant can result in the prosthetic implant becoming seized or at least partially retained in a position relative to tissue and/or one or more bones. In one embodiment, the outer smooth surface material of the prosthetic implant includes a wear resistant, relatively smooth material. The material may also have low frictional characteristics to allow for better movement between one or more bones and/or tissue. In another embodiment, the prosthetic implant is at least partially coated with a material that reduces or eliminates voids and/or non-smooth surfaces in the outer surface of the prosthetic implant. In one aspect of this embodiment, the coating is a biocompatible material. Materials of a biocompatible material that can be used include, but are not limited to, polytetrafluoroethylene, or polymers and/or co-polymers that include polytetrafluoroethylene. In another embodiment, the coated material is applied to the surface of the prosthetic implant by adhesive bonding, welding, soldering, shrink wrapping, melting, spray coating, hot dipping, electroplating, immersion coating, brush coating, and/or the like. The coated material can be biologically neutral or include one or more substances that inhibit bone and/or other tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In still another embodiment, the coating material enhances the strength and/or durability of the prosthetic implant and/or hardens or softens the surface of the prosthetic implant.

In accordance with yet another aspect of the present invention, the prosthetic implant includes one or more smooth surfaces to promote bone growth and/or other tissue growth into one or more smooth surfaces of the prosthetic implant. The one or more smooth surfaces allow for one or more smooth surfaces of the prosthetic implant to become partially or fully fused with one or more bones and/or tissues. The smooth surface can be designed to be adapted to engage and/or anchor to bone or tissue such as, but not limited to, vertebrae within the intervertebral disc space. In one embodiment, at least a portion of the surface of the prosthetic implant is coated with a material that forms a smooth surface. The coated material can be biologically neutral or can include one or more substances that promote bone or other tissue growth. In another embodiment, the coated material can be applied to the prosthetic implant by adhesive bonding, welding, soldering, shrink wrapping, melting, spray coating, hot dipping, electroplating, immersion coating, brush coating, and/or the like. The coated material can be biologically neutral or include one or more substances that promote bone and/or tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the prosthetic implant.

In accordance with still a further aspect of the present invention, the prosthetic implant includes one or more non-smooth surfaces and/or openings to promote bone growth and/or other tissue growth into the surface and/or interior of the prosthetic implant. The one or more non-smooth surfaces and/or openings allow one or more surfaces of the prosthetic implant to become partially or fully fused with one or more bones and/or tissues such as, but not limited to, vertebrae. The non-smooth surface can be designed to be adapted to engage with and/or anchor to the bone and/or tissue. In one embodiment, the non-smooth surfaces include, but are not limited to, ridges, ribs, grooves, pits, holes, notches, slits, slots, channels, corrugations, and the like. In another embodiment, at least a portion of the surface of the prosthetic implant is coated with a material that forms a non-smooth surface. The coated material is typically biocompatible; however, it not need be. In another embodiment, the coated material can be applied to the prosthetic implant by adhesive bonding, welding, soldering, shrink wrapping, melting, spray coating, hot dipping, electroplating, immersion coating, brush coating, and/or the like. The coated material can be biologically neutral or include one or more substances that inhibit bone and/or other tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the prosthetic implant.

In accordance with another aspect of the present invention, the prosthetic implant includes one or more internal cavities. These cavities can include one or more passageways to the outer surface of the prosthetic implant, or be at least partially isolated from the outer surface of the prosthetic implant. In one embodiment, at least one of the cavities is substantially vacant. In another embodiment, at least one of the cavities includes one or more substances that promote the effectiveness of the prosthetic implant in association with bone and/or tissue such as, but not limited to, the effectiveness of the prosthetic implant between at least two vertebrae. In one aspect of this embodiment, at least one of the substances include, but is not limited to, a substance which facilitates in the formation of a graft between one or more bones and/or a connection with one or more tissues. In another aspect of this embodiment, the substance can include, but is not limited to, medicine (e.g., cancer medication, infection medication, inflammation medication, pain medication, etc.), human tissue, animal tissue, synthetic tissue, human cells, animal cells, synthetic cells, tissue and/or bone promoters, inhibitors (e.g., rejection inhibitors), and/or visual and/or location indicators. In still another aspect of this embodiment, one or more cavities are filled with bone material or a synthetic material, with or without a bone activating matter, such as hydroxyapatite bone or proteins, bone growth factor, or cartilage activation factor. In still yet another embodiment, one or more of the cavities in the outer surface of the prosthetic implant allow blood supply and/or other body fluids to flow into and/or out of one or more of the cavities. In a further embodiment, the size or the passageway and/or opening to the outer surface of the prosthetic implant can be selected to control the amount and/or rate of the one or more substances in the one or more cavities that exit the cavities. In yet a further embodiment, the size or the passageway and/or opening to the outer surface of the prosthetic implant can be selected to control the amount and/or rate of bone and/or other tissue growth that occurs in the opening and/or passageway and into the one or more cavities. In still another embodiment, the substance in one or more cavities can be at least partially prepacked in the cavity prior to inserting the prosthetic implant into a human or animal, and/or the substance can be at least partially packed into one or more cavities after the prosthetic implant is inserted into a human or animal. In yet another embodiment of the invention, at least two of the cavities in the prosthetic implant intersect one another.

In accordance with still yet another aspect of the present invention, the prosthetic implant includes one or more openings in the outer wall to facilitate in the positioning of the prosthetic implant in a human or animal such as, but not limited to, insertion of the prosthetic implant between the vertebrae and/or to secure the prosthetic implant in place within the intervertebral disc space. In one embodiment, one or more of the openings in the outer wall of the prosthetic implant are adapted to receive an instrument for guiding and/or inserting the prosthetic implant into a human or animal. The one or more openings allow a surgeon to select the best approach for inserting the prosthetic implant in the human or animal. In one aspect of this embodiment, one or more of the openings in the outer wall of the prosthetic implant are adapted to receive an instrument for guiding the prosthetic implant between the vertebrae of the spine by an anterior, posterior, lateral, and/or latroscopic approach into the spinal column. In another embodiment, the instrument opening includes a securing mechanism such as, but not limited to, a thread, a slot, polygonal shaped opening, etc., to secure the instrument within the opening.

In accordance with still yet another aspect of the present invention, the prosthetic implant includes one or more openings in the outer wall of that can be at least partially closed prior to, during and/or after the prosthetic implant is inserted into a human or animal. In one embodiment, a cap is used to at least partially close one or more openings in the prosthetic implant. In one aspect of this embodiment, the cap substantially seals one or more openings. In another aspect of this embodiment, the cap alters the size of the one or more openings. The altered size of the one or more openings can be used to control the amount and/or rate of substances exiting the one or more openings and/or to control the rate and/or amount of substances, bone and/or other tissue entering the opening. In another aspect of this embodiment, the cap can be made of a porous material or a non-porous material. In another embodiment, the cap is adapted to receive an instrument for guiding and/or inserting the cap into one or more openings in the prosthetic implant. In still another embodiment, the cap is made of a biocompatible material. In one aspect of this embodiment, the cap is made or includes a material that is the same as the material make-up of the prosthetic implant. In another aspect of this embodiment, the cap is made of or includes a material that is different from the material of the prosthetic implant. In yet another embodiment, the cap is made of a material that fuses with the surrounding bone and/or tissue such as, but not limited to, a prosthetic implant inserted between one or more vertebrae. In yet another embodiment, the cap is made of a material that resists fusion with the surrounding bone and/or tissue while the prosthetic implant is between one or more bones. In still yet another embodiment, the cap is made of a material that decomposes after the prosthetic implant is positioned in a human or animal.

In accordance with another aspect of the present invention, the prosthetic implant is formed and/or modified based upon information obtained from the human or animal. In one embodiment, the prosthetic implant is designed, formed and/or modified to a custom shape and/or size within a medical facility or in a facility relatively close to a medical facility while the patient is in surgery or at a relatively short time prior to patient entering into surgery. Typically, smaller prosthetic implants such as, but not limited to, cages to be inserted into the intervertebral disk space, are stocked or available in greater qualities at a medical facility. Generally, these cages are manufactured in certain standard shapes and sizes. Due to storage and inventory limitations at a medical facility and the costs involved in maintaining large inventories, the closest size cage may not be available for the patient during surgery, thus the best available cage is used. As a result, the patient may experience more pain and/or less mobility than if the best sized cage had been available for use. Furthermore, even when the best available cage size is available, such standard cage may still deviate substantially in shape and/or size thereby resulting in irritation to the patient, and other mobility and/or movement problems due to the imprecise size and/or shape of the prosthetic implant. For larger prosthetic implants, it is also common to obtain a standard shaped and sized prosthetic implants. Typically, these larger standard sized prosthetic implants are less readily availability, thereby requiring additional time for acquisition. Many of the larger prosthetic implants are formed of metal and require custom casts to manufacture. Due to the expense involved in manufacturing and maintaining an inventory of different sized casts, the facilities that make the prosthetic implants only maintain a certain size range of casts. As a result, the prosthetic implant is manufacture using a cast size that most closely approximates the desired size. Furthermore, the shapes of the casts are selected to approximate an average shape. Some individuals have bones and/or spaces that significantly deviate from the average shape. As a result, many of the produced prosthetic implants are not the exact size and/or shape of the bone and/or tissue being replaced in a particular patient. Furthermore, the surgeon has little ability to modify the prosthetic implant due to the material hardness of the prosthetic implant and/or lack the skill and/or tools necessary to modify the shape and/or size of the produced prosthetic implant. As a result, the use of these standard sized and shaped prosthetic implants may still deviate substantially in shape and/or size thereby resulting in irritation to the patient, and other mobility and/or movement problems due to the imprecise size and/or shape of the prosthetic implant. Consequently, the insertion of the prosthetic implant into the patient, though improving the situation prior to the insertion of the prosthetic implant, can result in irritation to the patient, and other mobility and/or movement problems due to the imprecise size and/or shape of the prosthetic implant. Custom shaped and sized prosthetic implants can be obtained for a patient. Presently, custom sized prosthetic implants take several days to several months to produce. As a result, a patient must first visit the medical facility for examination to obtain an approximate size for the prosthetic implant. Once the measurements are obtained, the prosthetic implant is ordered and the patient must wait until delivery of the prosthetic implant. This delay in obtaining a prosthetic implant exists both for patients that have recently receive injury or damage to one or more bones and/or tissue, and to patients that require bone replacements, disk replacements and the like to minimize pain and/or mobility problems due to age, minor injuries, bone abnormalities and the like. Even after the custom shaped prosthetic implant is obtained, there may still exist some deviations in the shape and size of the custom prosthetic implant. Typically, the surgeon has little ability to modify the custom sized prosthetic implant. As a result, the use of these prosthetic implants may still deviate substantially in shape and/or size thereby resulting in irritation to the patient, and other mobility and/or movement problems due to the imprecise size and/or shape oft he prosthetic implant. The present invention overcomes these past limitations of obtaining the desired shape and/or size of a prosthetic implant and further overcomes the problems associated with obtaining such prosthetic implant in a shorter time frame without having a medical facility maintain extensive inventories of prosthetic implants. The basic concept of the invention is a process and method for manufacturing a prosthetic implant by 1) obtaining information from the patient about the size and/or shape of desired the prosthetic implant, and 2) forming a prosthetic implant based upon the size and/or shape information by use of a moldable compound. By use of a moldable compound, the prosthetic implant can be better matched to a particular use, size, and/or shape. In addition, since the prosthetic implant is at least partially made from a moldable compound, the need to maintain vast inventories of prosthetic implants is eliminated. Finally, the time necessary to manufacture a particular prosthetic implant is significantly reduced by using a moldable compound.

In accordance with still another aspect of the present invention, the information obtained for the size and/or shape of the prosthetic implant is taken by commonly available medical techniques. In one embodiment, the size and/or shape information for the prosthetic implant are at least partially taken by techniques that do not require incisions into the body of the human or animal. These techniques include, but are not limited to, X-ray, ultrasound, MRI, cameras, scopes, and the like, and/or by physical measuring of the region that includes the bone and/or tissue to be partially or fully replaced by the prosthetic implant. In another embodiment, the size and/or shape information for the prosthetic implant are at least partially taken by techniques that require incisions into the body of the human or animal. These techniques include, but are not limited to, surgical removal of the bone and/or tissue to be repaired and/or replaced, surgical incisions to provide access to the bone and/or tissue to be repaired and/or replaced. In another embodiment, the acquired information for the size and/or shape of the prosthetic implant is inputted into a data processor such as a microprocessor to enable the data processor to at least partially generate two and/or three-dimensional information and/or data points, and/or two and/or three-dimensional images of the prosthetic implant to be manufactured. In one aspect of this embodiment, a scanned image of the bone and/or tissue to be repaired and/or replaced by the prosthetic implant is processed by one or more microprocessors to at least partially generate two and/or three-dimensional data points, and/or two and/or three-dimensional images of the prosthetic implant to be manufactured. In another aspect of this embodiment, data generated by an MRI, ultrasound or the like is processed by one or more microprocessors to at least partially generate two and/or three-dimensional data points, and/or two and/or three-dimensional images of the prosthetic implant to be manufactured. In still another aspect of this embodiment, generated two and/or three-dimensional data points, and/or two and/or three-dimensional images of the prosthetic implant are compared to the acquired information used to generate the data points and images of the prosthetic implant to determine the accuracy of the generated data points and/or images and/or to allow the generated data points and/or images to be modified prior to the production of the prosthetic implant. In one preferred application of the invention, a patient's body is at least partially scanned by an MRI and/or ultrasound device and/or imaged by an X-ray machine to obtain an image of the bone and/or tissue to be repaired and/or replaced by the prosthetic implant. The image is then further processed by one or more microprocessors to generate a three-dimensional image and data points for the three-dimensional image of the prosthetic implant that is to be used to repair and/or replace the bone and/or tissue in the patient. After the data points and image have been generated, the image is compared to the image of the bone and/or tissue obtained by the MRI and/or ultrasound device and/or X-ray machine to assess the accuracy of the generated image of the prosthetic implant. After the images have been compared, the generated data points and image are modified, if necessary.

In accordance with still another aspect of the present invention, information of and/or relating to the two and/or three-dimensional data points and/or images of the prosthetic implant are transferred to a molding machine, which molding machine at least partially produces the prosthetic implant. In one embodiment, the information is electronically transmitted to the molding machine and/or manually inputted into the molding machine. In another embodiment, additional information is transferred to the molding machine. This additional information can include, but is not limited to, type of material to be used to form the prosthetic implant, cavities to be included in the prosthetic implant, surface features of the prosthetic implant, connectors to be included on the prosthetic implant to facilitate in the insertion of the prosthetic implant into a patient, secondary structures to be included in the prosthetic implant, frame and/or support structures use to at least partially form the prosthetic implant, the day and/or time the prosthetic implant is to be manufacture, the patient's name, the medical facility's name, the physician's name, the medical procedure to be used to insert the prosthetic implant, the location within the patient's body at which the prosthetic implant is to be inserted, the date of implant of the prosthetic implant, the machine used to form manufacture the prosthetic implant, the machine and/or name of individual used to generate the data that was transferred to the molding machine, additives to be included in the prosthetic implant, modifications to the prosthetic implant, approval codes or signatures, etc. As can be appreciated, some or all of this additional information can be made a part of the information that was initially transferred to the molding machine. In one aspect of this embodiment, some or all of this information can be molded, printed, cut, etched and/or stamped on the formed prosthetic implant and/or the packaging of the prosthetic implant and/or input into a computer chip or smart chip to be inserted into the implant during the molding process. In still another embodiment, the molding machine forms the prosthetic implant based upon some or all of the information transferred to the molding machine. In one aspect of this embodiment, the molding machine automatically produces the prosthetic implant after receiving the transferred information or on a preselected date. In another aspect of this embodiment, a physician and/or technician causes the molding machine to form the prosthetic implant after the needed information for the prosthetic implant has been transferred to the molding machine.

In accordance with still another aspect of the present invention, the molding machine is designed to produce a single type of prosthetic implant or can form various types of prosthetic implants. In one embodiment, the molding machine is designed to form certain types of prosthetic implants. For instance, the molding machine can be designed to only form prosthetic implants for insertion in the intervertebral disk space. The molding machine can be even further limited to form only one or a few types of prosthetic implants for insertion in the intervertebral disk space. In another embodiment, the molding machine is designed to form a wide variety of shaped and sized prosthetic implants. In one aspect of this embodiment, the molding machine can form prosthetic implants for all the bones and tissue in a human or animal. In another aspect of this embodiment, the molding machine can form prosthetic implants for all bones and/or tissue in a certain region of the body of a human or animal. In still another aspect of this embodiment, the molding machine can form prosthetic implants for all bones and/or intervertebral disk spaces forming the vertebrae. In yet another aspect of this embodiment, the molding machine can form prosthetic implants for one or more of the intervertebral disk spaces of the vertebrae of a human or animal.

In accordance with yet another aspect of the present invention, the molding machine can accept one or more different moldable materials to at least partially form the prosthetic implant. In one embodiment, the molding machine is designed to use only a certain type of moldable material. In another embodiment, the molding machine is designed to use only a certain viscosity range of moldable materials. In still another embodiment, the molding machine is designed to at least partially form molds of prosthetic implants from a wide variety of different moldable compounds and/or a wide range of viscosities of moldable compounds. In a still yet another embodiment, the molding machine is designed to at least partially form molds of prosthetic implants by use of one or more moldable compounds. Different parts of a human or animal are subject to different loads and stresses. As a result, different compounds used to make the prosthetic implants may be more beneficial in certain regions of the human or animal than other regions. Consequently, the molding machine can be specifically designed to only use certain moldable compounds for production of certain prosthetic implants. Such a molding machine may be less expensive to manufacture and maintain. Furthermore, because a limited number of moldable compounds would be used in such molding machine, the time and expense of cleaning and prepping the molding machine prior to forming other prosthetic implants may be reduced. Medical facilities or medical facility suppliers that specialize in certain medical procedures that involve a limited body location (e.g., spinal surgery and products associated therewith) may desire a molding machine that is specially designed to form prosthetic implants for their particular specialized area since such a machine may be potential smaller and less expensive. In another embodiment, the molding machine is designed to accommodate a variety of different moldable compounds. Such a molding machine could produce most, if not all, of the various types of prosthetic implants for a human or animal. This molding machine would eliminate the need for multiple molding machines that are designed only to make certain types of prosthetic implants and/or molding machines designed only to use limited types of moldable compounds. The molding machine would most benefit medical facilities that deal with a wide variety of injuries such as a hospital, orthopedic facility, and/or a prosthetic supplier for a hospital or orthopedic facility.

In accordance with yet another aspect of the present invention, the moldable compound is a compound consisting of one or more substances that can be formed or shaped. In one embodiment, the moldable compound is a liquid or semi-solid compound. In one aspect of this embodiment, the viscosity of the moldable compound allows the moldable compound to be flowed into a mold. In another aspect of this embodiment, the viscosity of the moldable compound is such that the moldable compound cannot be flowed into a mold, thus must be placed into the mold and then subjected to temperature, environmental and/or pressure changes to form the moldable compound in the mold. In still another aspect of this embodiment, the viscosity of the moldable compound allows the moldable compound to be extruded to form or partially form the prosthetic implant. In another embodiment, the moldable compound is a solid compound. In this aspect of the embodiment, the moldable compound is placed into the mold and then subjected to temperature, environmental and/or pressure changes to form the moldable compound in the mold. In still another embodiment, the moldable compound, whether in liquid, semi-liquid, gas or solid form, is subjected to one or more catalysts or activation compounds of the like to cause a chemical activation to begin and/or accelerate thereby resulting in the moldable compound to become more moldable, less moldable, structurally different, etc. In still another embodiment, the moldable compound includes, but is not limited to, albumin microspheres; alginates; apatite-wollastonite containing glass ceramic-fibrin; bone; calcium phosphate compounds (e.g., alpha-tricalcium phosphate compounds, beta-tricalcium phosphate compounds, whitlockite compounds, tribasic calcium phosphate compounds, hydro-xyapatite, dentin, tricalcium phosphate-gelatin mixtures, tricalcium phosphate-gelatin-glutaraldehyde mixtures, etc.); ceramics (zirconium oxide ceramic, aluminum oxide ceramic, etc.); chitosan compositions, collagen compounds (e.g., collagen, methylated collagen, gelatinized collagen, etc.); fibrin; fibrocartilage or other cartilage, fibrinogen; gelatin; liposomes; lipids with emulsifiers; metals (e.g., chrome, chrome alloys (e.g., chromemolybdenum), cobalt, cobalt alloys (e.g., cobalt chromium alloy), stainless steel, titanium, etc.); marine adhesive proteins; pegulated marine adhesives; pegulated particulate; polymers, co-polymers, resins, and/or thermoplastics (e.g., cyanoacrylates, lactides, lactide/glycolide copolymers, polyamides, polycarbonate, polydioxamone, polyethylene, polyethylene glycol, polyesters, polyglycolate, polymethylmethacrylate, polyorthoesters, polypropylene, polysolfone types filled with glass and/or carbon fibers, polytetrafluoroethylene, polyvinyl alcohols, carbon and fiber reinforced polymers and/or resins, urethanes, etc.); proteins in solid state (e.g., albumin powder, etc.); pyrrolidone; silica compounds; and/or silicon compounds. In one aspect of this embodiment, the moldable compound includes calcium phosphate compounds, ceramics, metals, polymers, co-polymers, resins, and/or thermoplastics. In one specific embodiment, the moldable compound has a generally soft putty property that allows the moldable compound to be easily form, and if necessary, allows the moldable compound to be extruded, and/or flowed into and/or through a mold. Some specific examples of components of the moldable compound that can be used include, but are not limited to, methylmerthacolate, tricalciumphosphate offered under the mark NORION, resin compounds offered under the mark CORTOSS, silica compounds offered under the mark FILTEK and SILUX, and ceramic compounds offer under the mark P-10.

In accordance with yet another aspect of the present invention, the prosthetic implant includes one or more biological additives to increase the success of the implanted prosthetic implant and/or to address one or more related and/or unrelated biological processes. In one embodiment, the moldable compound used in the prosthetic implant includes one or more biological additives. In another embodiment, one or more structures that form the prosthetic implant other than the moldable compound include one or more biological additives. In still another embodiment, one or more biological additives are coated onto at least a portion of the surface of the prosthetic implant. In still yet another embodiment, one or more biological additives are inserted into one or more cavities of the prosthetic implant. In still yet another embodiment, the biological additive includes, but is not limited to, compounds that promote or repress growth of bone and/or tissue about the prosthetic implant, reduce pain, reduce inflammation, promote healing, and/or to prevent infection. In one aspect of this embodiment, the biological additive includes, but is not limited to genes encoded with biologically useful proteins (e.g., growth hormone); growth hormone releasing factor; pituitary factors; adrenal factors; pancreatic factors; interferon factors; prostaglandin releasing factors; hormones (e.g., progesterone, testosterone, follicle simulating hormone (FSH), insulin, and somatotropins); antihistamines (e.g., diphenhydramine and chlorphencramine); cardiovascular agents (e.g., digitalis, nitroglycerine, papaverine and streptokinase); anti-ulcer agents (e.g., cimetidine hydrochloride, and isopropamide iodide); bronchodilators (e.g., metaprotemal sulfate and aminophylline); vasodilators (e.g., theophylline, niacin and minoxidil); central nervous system agents (e.g., tranquilizers, b-adrenergic blocking agents, and dopamine); antipsychotic agents (e.g., risperidone and olanzapine); narcotic antagonists (e.g., naltrexone, nalbxone and buprenorphine); nerve growth promoting substances (e.g., ganglioside or a nerve growth factor); hard or soft tissue growth promoting agents (e.g., fibronectin (FN), human growth hormone (HGH), recombinant human bone morphogenic proteins (rhBMPs), colony stimulating factors (CSFs), nerve growth factors (NGF), brain-derived neurotropic factor (BDNF), ciliary neurotropic factor (CNTF), bone morphogenic protein, platelet-derived growth factor (PDGF, PDGF-AA, PDGF-AB, PDGF-BB), insulin-derived growth factor (IGF-I, IGF-II), transforming growth factor-alpha (TGF-.alpha.), transforming growth factor-.beta. (TGF-.beta, TGF-.beta.-2), epidermal growth factor (EGF), fibroblast growth factor (FGF), interleukin-1 (IL-1)); prostaglandins (e.g., PGE.sub.1, PGE.sub.2 and PGD.sub.2); antineoplastic agents (e.g., methotrexate, 5-fluouracil, adriamycin, vinblastine, cisplatin); tumor-specific antibodies conjugated to toxins; tumor necrosis factors (TNF); therapeutic agents (e.g., cytokines, interleukins (IL-1, IL-2) or other co-factors such as heparin or calmodulin, antibiotics, antineoplastic and antibacterials); antibacterial agents (e.g., penicillin, cephalosporins, bacitracin, tetracycline, doxycycline, gentamycin, quinolines, neomycin, clindamycin, kanamycin, and metronidazole); anti-inflammatory agents (e.g., hydrocortisone, and prednisone; antiparasitic agent such as quinacrine, chloroquine, and vidarbine); antifungal agents (e.g., nystatin); antiviral agents (e.g., acyclovir, ribarivin, and interferons); analgesic agents (e.g., salicylic acid, acetaminophen, ibuprofen, naproxen, piroxicam, flurbiprofen, and morphine); local anesthetics (e.g., lidocaine, bupivacaine and benzocaine); immunogens (vaccines); and/or peptides (e.g., leuprolide acetate (an LH-RH agonist), nafarelin, and ganirelix).

In accordance with a further aspect of the present invention, the prosthetic implant includes one or more cells to promote growth of bone and/or tissue about the prosthetic implant. In one embodiment, the cells include, but are not limited to, chondrocytes, osteocytes, osteoblasts, osteoclasts, mesenchymal stem cells, fibroblasts, muscle cells, hepatocytes, parenchymal cells, cells of intestinal origin, nerve cells, and/or skin cells. In another embodiment the moldable compound used in the prosthetic implant includes one or more cells. In another embodiment, one or more structures that form the prosthetic implant other than the moldable compound include one or cells. In still another embodiment, one or more cells are coated onto at least a portion of the surface of the prosthetic implant. In still yet another embodiment, one or more cells are inserted into one or more cavities of the prosthetic implant.

In still a further embodiment, the molding machine forms the prosthetic implant using only the moldable compound or using the moldable compound in combination with one or more preexisting structures. In one embodiment, the prosthetic implant is at least substantially formed from the moldable compound. In this embodiment, the principal structure of the prosthetic implant is formed from the moldable compound. In one aspect of this embodiment, the prosthetic implant is stamped from the moldable compound, extruded from the moldable compound, formed in a mold using the moldable compound, and/or cut from the moldable compound (e.g., mechanical cutting, laser cutting, fluid cutting, etc.). In another embodiment, the prosthetic implant includes one or more structural frames upon which the moldable compound is at least partially coated and/or at least partially positioned in the one or more frame structures. The one or more structures and/or frames are used to provide a partial or full shape for the prosthetic implant, used to form passageways and/or cavities in the prosthetic implant, and/or used to provide structural support for the prosthetic implant. The size and/or shape of the structures and/or frames can be selected at least partially based upon the information taken from the patient. As such, a closely sized standard structure and/or frame can be transformed into a custom sized and/or shaped prosthetic implant by at least partially coating the structure and/or frame with the moldable compound. As can be appreciated, other physical properties and/or features of the standard structure and/or frame can be selected based at least partially based upon the information taken from the patient. In one aspect of this embodiment, the prosthetic implant for a femur is formed by coating a metal or fiber rod with the molding compound. In this aspect of the embodiment, the metal or fiber rod at least partially functions as a support structure to provide strength and rigidity to the prosthetic implant. The moldable compound is coated onto the rod to cause the shape of the prosthetic implant to better simulate the actual shape of the femur to be partially or fully replaced in the patient's body. The moldable compound is also used to customize the shape of the prosthetic implant for a particular patient even if a generically shaped rod is used. As such, the moldable compound can be used to lengthen the prosthetic implant, better shape the joints of the prosthetic implant, etc. The moldable compound can also impart strength and rigidity to the prosthetic implant. The moldable compound can also include compounds that will resist wear of the prosthetic implant so as to increase the life of the prosthetic implant. The moldable compound can also include compounds that will increase the acceptance of the prosthetic implant and/or promote healing about the prosthetic implant. In another aspect of this embodiment, the prosthetic implant for an intervertebral disk includes a preexisting cage that is coated with the molding compound. In this aspect of the embodiment, the cage partially functions as a support structure to provide strength and rigidity to the prosthetic implant. The cage also provides the general shape for the prosthetic implant. The moldable compound is coated onto the cage to form a customize prosthetic implant for an intervertebral disk space of a particular patient. As such, a generically shaped cage can be used and transformed by the moldable compound into a prosthetic implant having the particular dimensions for an intervertebral disk space of a particular patient. The moldable compound can also impart strength and rigidity to the prosthetic implant. The moldable compound can also include compounds that will resist wear of the prosthetic implant so as to increase the life of the prosthetic implant.

In still a further embodiment, the prosthetic implant that is at least partially formed from a moldable compound includes one or more secondary structures. The secondary structures can be inserted onto the prosthetic implant after the moldable compound has been formed, and/or one or more secondary structures can be included in the prosthetic implant at the time or prior to the time the moldable compound is formed. In one embodiment, the secondary components include, but are not limited to, screw openings, rods, plates, screws, connectors, mounts, joints, and/or the like. In one aspect of this embodiment, the prosthetic implant includes rods, screws, etc. that extend from one or more surfaces of the prosthetic implant. The rods, screws, etc. are used, but are not limited to only such use, as structures that anchor and/or connect the prosthetic implant to tissue and/or bone in the human or animal. In another aspect of this embodiment, the screw openings, mounts, connectors, etc. are used, but are not limited to only such use, as structures that connect and/or attach the prosthetic implant to bone and/or tissue in a human or animal, connect and/or attach the prosthetic implant to another prosthetic implant, connect and/or attach the prosthetic implant to shafts, rods, plates, wires and other devices used for insertion of the prosthetic implants into a human or animal, and/or to secure the prosthetic implant in place in a human or animal. In still another aspect of this embodiment, the rods, plates, joints, etc. are used to structurally enhance the prosthetic implant, form part of the shape of the prosthetic implant, etc. In one specific design, the secondary structure includes a joint that is connected to one part of the prosthetic implant. The joint may or may not be made of the same material as the remainder of the prosthetic implant. For instance, if the prosthetic implant was for a femur, the joint can be for the head and/or neck of the femur. In this design, the joint can be made or a special durable material that would resist wear when in contact with the ilium. Similar designs can be incorporated with other bones and/or tissue. In still yet another aspect of this embodiment, the secondary structures can be used to modify the size and/or shape of the prosthetic implant. In one aspect of this embodiment, the prosthetic implant includes one or more pins and/or screws that are used to change the size and/or shape of the prosthetic implant after the prosthetic implant has been molded. For instance the pins and/or screws can be turned or otherwise moved to change the size and/or shape of one or more regions of the prosthetic implant (e.g., narrow, widen, lengthen, and/or shorten).

In another embodiment, the moldable compound of the prosthetic implant is fully or partially hardened prior to inserting the prosthetic implant into a human or animal. The moldable compound can be hardened by one or more techniques such as, but not limited to, heat, drying, radiation, catalysts, chemical reactions, other electromagnetic waves (e.g., ultraviolet light, inferred light, visible light, microwaves, radio waves, X-rays, gamma rays, etc.), sound waves (e.g., audible sound, ultrasonic waves), and the like. In one embodiment, the moldable compound in a partially hardened state allows a surgeon to make minor modifications to the prosthetic implant while the prosthetic implant is inserted into the patient. In one aspect of this embodiment, a portion of the prosthetic implant is substantially hardened and a portion of the prosthetic implant is not fully or substantially hardened. In one specific design, the prosthetic implant is a portion of a rib. The end of the prosthetic implant that is to merge with an existing rib is not fully hardened. Once the prosthetic rib is positioned in the patient, the non-hardened portion of the prosthetic implant is at least partially molded by the surgeon onto the existing rib. After the molding by the surgeon, the non-fully hardened moldable compound can be hardened by the surgeon and/or be left in the patient to harden or not harden on its own.

In still another embodiment, the prosthetic implant is subsequently processed after being formed in the molding machine. The subsequent processing can include, but is not limited to, labeling, laser cutting, smoothing, minor sizing, disinfecting, etching, etc. In one embodiment, the prosthetic implant is labeled to provide information about the implant. The label can include, but is not limited to, a printed bar code, computer chip, ink or impression stamping, paper label, etching, etc. In another embodiment, the prosthetic implant is physically altered to further customize the shape of the prosthetic implant. In one aspect of this embodiment, the prosthetic implant is polished, sanded, cut, etc. to smooth and/or alter one or more surfaces of the prosthetic implant. In another aspect of this embodiment, the prosthetic implant is etched and/or subjected to a fluid environment to caused one or more exterior and/or interior surfaces of the prosthetic implant to be removed. In one aspect of this embodiment, the prosthetic implant is at least partially formed from a frame, that when subjected to a fluid, is dissolved or otherwise removed to form one or more cavities and/or passageways in the interior and/or exterior of the prosthetic implant. In still another embodiment, the prosthetic implant is subjected to a fluid environment to clean, disinfect and/or sanitize one or more surfaces of the prosthetic implant.

In still yet another embodiment, there is provided a method for producing a prosthetic implant that can be customized to size and/or shape in a limited amount a time without the need for a facility to stock large quantities of various sized prosthetic implants. The method contemplates the production of prosthetic implants used to partially or fully replace a bone, and/or prosthetic implants used to partially or fully replace tissue such as, but not limited to, ligaments or cartilage (e.g., nose, ear, joints, intervertebral disks, etc.). The method generally involves two steps, namely 1) obtaining information about the bone and/or tissue to be at least partially replaced by the prosthetic implant and/or obtaining information concerning the region about which the implant is to be inserted, and 2) at least partially molding the moldable compound in a molding machine to at least partially form the prosthetic implant. In one embodiment, the information obtained for the production of the prosthetic implant is at least partially obtained mechanically (e.g., ruler, imprint, etc.), chemically (e.g., chemical analysis, spectral analysis, atomic analysis, etc.), and/or electronically (e.g., MRI, X-ray, ultrasonic waves, photography, etc.). In another embodiment, the moldable compound is a non-hardened moldable compound which becomes hardened or less moldable when subjected to one or more mechanical processes (e.g., heat, pressure, drying, sound and/or ultrasonic waves, etc.), catalytic processes (e.g., light, sound and/or ultrasonic waves, electric current, radiation, other electromagnetic waves, etc.), and/or chemical processes (e.g., reaction with the one or more added chemical substances). In one aspect of this embodiment, the moldable compound includes, but is not limited to, one or more compounds selected from the group of mineralized collagen, bone growth materials, bone proteins, powdered or harvested bone, biomaterials, chopped carbon and/or inert materials, polymers that convert from a moldable to an at least partially non-moldable state when subjected to a mechanical process and/or chemical A process, metals and metal alloys (including shape memory alloys). In still another embodiment, the molding machine at least partially forms the prosthetic implant by use of a mechanical, catalytic, and/or chemical process. In yet another embodiment, at least a portion of the prosthetic implant is coated and/or impregnated with one or more substances. These substances include, but are not limited to, chemical compounds that modify one or more physical properties (e.g., color, hardness, wear resistance, etc.) of the prosthetic implant, and/or biological additives. In still yet another embodiment, the prosthetic implant is at least partially coated with a bone growth enhances to simulate bone growth and/or enhance fixation of the prosthetic implant onto/into the bone. The coating process can occur immediately after the formation of the prosthetic implant, prior to implanting the prosthetic implant into a patient, and/or during and/or after the prosthetic implant is inserted into the patient. In a further embodiment, one or more components are affixed to the surface of the prosthetic implant. These components can be inserted during and/or after the molding of the prosthetic implant. In one aspect of this embodiment, the components include cylindrical, polygonal, etc., shaped extensions having either male threaded ends or inner cavities to receive male threaded ends for use in affixing the prosthetic implant to bone and/or tissue, and/or for inserted the prosthetic implant into the patient. In yet a further embodiment, the prosthetic implant is shaped and/or sized to form a custom-sized prosthetic implant. In one aspect of this embodiment, the prosthetic implant is a custom-sized spinal fusion implant. In one specific example, the method includes the production of a custom-sized disc for a patient's back in which spinal fusion on the patient is to be performed wherein measurements of the spinal disk space are taken while a) the patient is anesthetized, b) before surgery by an MRI or other radiological or other pre-surgical procedure, c) by percutaneous measurement or other non-radiological procedures during the surgical procedure, or (d) by other non-radiological procedures (e.g., sonar, radar, ultrasound, etc.). The measurements are taken by mechanical and/or electronic measuring devices, which measure the needed dimensions of the spinal fusion implant in three dimensions. The measurements are then utilized by the surgeon to select from amongst various sized "molds" to pick the appropriate sized mold for the spinal fusion implant. The mold is used in combination with other devices (e.g., shims; spacers to expand, confine or otherwise shape the mold), which will be injected with a moldable compound to create the custom-sized spinal fusion implant. Alternatively, the measurements are transmitted to a molding device which is mechanically and/or electronically set to form the spinal fusion implant with the desired dimensions so that the moldable compound can be injected into the mold to create the custom-sized spinal fusion implant. Alternatively, the measuring device can be connected to an injection nozzle that injects a liquid moldable compound into the dimensioned mold cavity to form the custom-sized spinal fusion implant. The mold for the custom-sized spinal fusion implant can form a solid implant or include one or more structures that form a spinal fusion implant with one or more cavities or internal channels. These one or more structures can be designed to be removed from the molded implant to form openings, cavities and/or channels in the implant so that such structures can a) be used to properly position the implant by use of tools into the patient, b) be packed with various materials such as, but not limited to, i) mineralized collagen designed to enhance bone growth, ii) other bone growth material, iii) powered or harvested bone (e.g., from the patient or other sources), iv) other biomaterials, and/or v) chopped carbon and/or other inert materials. In another aspect of this embodiment, the prosthetic implant is a custom-sized spacer that can be used in orthopedic surgery for the purpose of distracting a space between two bony surfaces and/or to act as a spacer between such surfaces.

It is the principal object of the present invention to manufacture a custom-sized prosthetic implant.

It is another and/or alternative object of the present invention to at least partially form the custom-sized prosthetic implant from a moldable compound.

It is still another and/or alternative object of the present invention to at least partially form the custom-sized prosthetic implant in a molding machine using a non-hardened moldable compound.

It is yet another and/or alternative object of the present invention to at least partially form the custom-sized prosthetic implant from a modified mold.

It is still yet another and/or alternative object of the present invention to obtain measurements from a patient and use such measurements to at least partially form the custom-sized prosthetic implant.

It is still another and/or alternative object of the present invention to provide a custom-sized prosthetic implant for insertion between two vertebrae.

It is another and/or alternative object of the present invention to provide a custom-sized prosthetic implant which at least partially emulates the space between the vertebrae.

Still another and/or alternative object of the present invention is to provide a prosthetic implant that can be used as a partial or full replacement for bones and/or other tissue in a human or animal.

Yet another and/or alternative object of the present invention is to provide a custom-sized prosthetic implant which includes one or more non-smooth surfaces.

It is still yet another and/or alternative object of the present invention to provide a custom-sized prosthetic implant which provides improved support, fixation and methodology which provides stability and in which the shape will facilitate in securing the prosthetic implant to bone and/or tissue.

Yet a further and/or alternative object of the present invention is to provide a custom-sized prosthetic implant that includes one or more smooth surfaces to inhibit bone and/or other tissue growth on the smooth surface.

Still yet another and/or alternative object of the present invention is to provide a custom-sized prosthetic implant that includes a cap to at least partially alter the size of an opening in the outer surface of the prosthetic implant.

Another and/or alternative object of the present invention is to provide an apparatus which will at least partially aid in the positioning of the custom-sized prosthetic implant in a patient.

Still yet another and/or alternative object oft he present invention is to provide a custom-sized prosthetic implant which has one or more openings that can receive packing material to facilitate in the fusion with one or more bones and/or the healing process after insertion of the prosthetic implant.

A further and/or alternative object of the present invention is to provide a custom-sized prosthetic implant which can be easily and efficiently positioned in a patient and which reduces the failure rate of prosthetic implant.

It is still another and/or alternative object of the present invention to provide a custom-sized prosthetic implant which includes one or more surfaces that reduce pinching and/or irritation with surrounding bone and/or tissue.

It is still yet another and/or alternative object of the present invention to provide a custom-sized prosthetic implant that is at least partially made of a biologically compatible material.

It is another and/or alternative object of the present invention to provide a custom-sized prosthetic implant that is at least partially made of and/or includes a material that enhances the visibility of the implant when exposed to X-rays, sound waves, light waves, magnetic waves, and/or various other types of electromagnetic waves.

It is still another and/or alternative object of the present invention to provide a custom-sized prosthetic implant that is at least partially made of a material which closely approximates the elasticity of replaced bone and/or tissue.

It is yet another and/or alternative object of the present invention to provide a custom-sized prosthetic implant that includes one or more structures that enhance the strength and/or durability of the prosthetic implant.

It is still yet another and/or alternative object of the present invention to provide a custom-sized prosthetic implant that includes at least one structure that facilitates in securing the prosthetic implant to bone, tissue and/or other structures about the bone and/or tissue.

It is still another and/or alternative object of the present invention to provide a method of producing a custom-sized prosthetic implant that significantly reduces the time of such manufacture.

It is yet another and/or alternative object of the present invention to provide a method of producing a custom-sized prosthetic implant that reduces the need for a medical facility to stock a vast number of prosthetic implants.

It is still yet another and/or alternative object of the present invention to provide a method of producing a custom-sized prosthetic implant that is economical to produce.

It is a further and/or alternative object of the present invention to provide a method of producing a custom-sized prosthetic implant that is simpler to produce.

It is another and/or alternative object of the present invention to provide a method of producing a custom-sized prosthetic implant at least partially from a frame or structure.

It is another and/or alternative object of the present invention to provide a method of producing a custom-sized prosthetic implant that further modifies the shape and/or size of the produced prosthetic implant after being removed from the mold.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings that form a part hereof and wherein.

DESCRIPTION OF THE PREFERRED EMBODIMENTS

Figure 1:
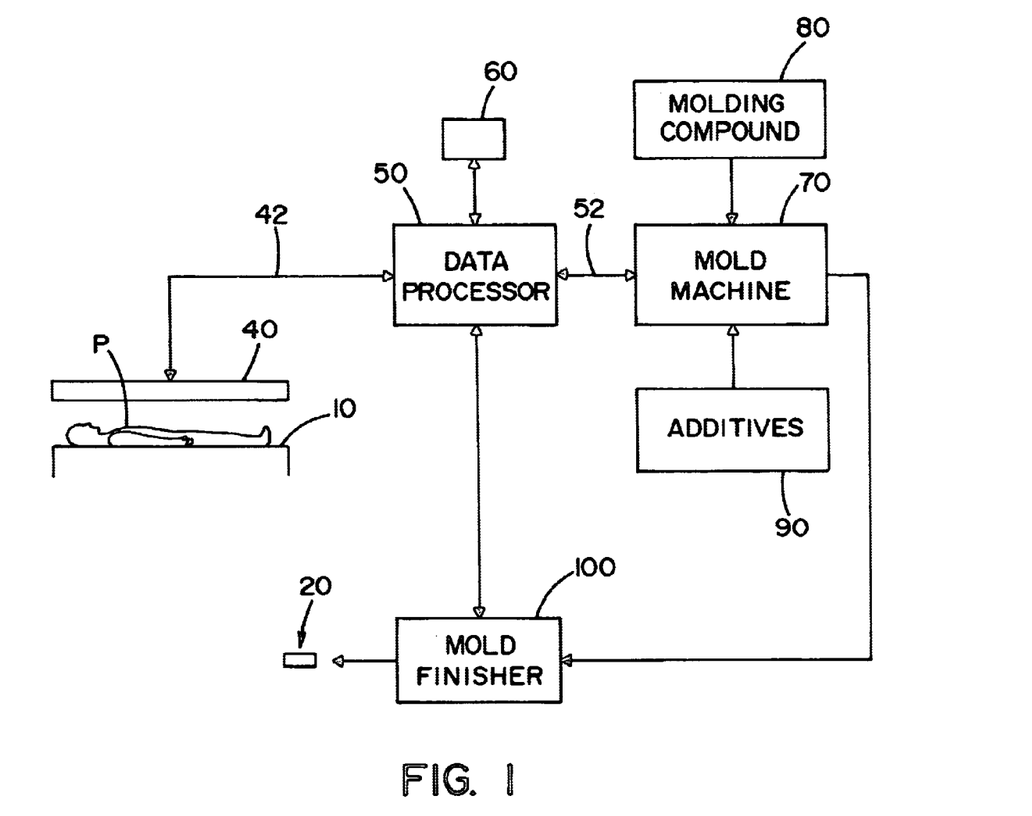
FIG. 1 is a block diagram illustrating a process for producing a custom-sized prosthetic implant of the present invention.

Referring to the drawings, wherein the showings are for the purpose of illustrating the preferred embodiment of the invention only and not for the purpose of limiting the same, FIG. 1, illustrates one of the manufacturing processes for producing a custom-sized prosthetic implant in accordance with the present invention. As illustrated in FIG. 1, patient P is positioned on an examining table 10 for examination to obtain information about the size and shape of a prosthetic implant 20 to be surgically implanted into the patient. A scanning device 40 is positioned near the patient to obtain information concerning the region about which the prosthetic implant will be inserted into the patient. The scanning device can be any number of devices such as, but not limited to an MRI, an ultrasonic scanner, and inferred scanner, a radiation scanner, a heat scanner, an X-ray machine, and the like. As can be appreciated, one scanning device or multiple scanning devices can be used to obtain the data required for the prosthetic implant. In one typical arrangement, the scanning device is an MRI.

After the scanning device has completed the scan of the patient and/or during the scan of the patient, data from the scanning device is transmitted to a data processor 50. The data processor can be a hard wired circuit, and/or be one or more computers or the like. As illustrated in FIG. 1, the data from the scanning device is electronically transmitted via cable or wire 42. As can be appreciated, a portion or all of the data from the scanning device can be manually inputted into data processor 50. Furthermore, the data can be fully or partially transmitted to data processor 50 by radio waves, microwaves and the like. The data from the scanning device is processed by the data processor to generate information for forming a multi-dimensional prosthetic implant. One or more pieces of hardware and/or software are used to generate the information for forming the multi-dimensional prosthetic implant. As shown in FIG. 1, the data processor is designed to send information to the scanning device; however, such communication is not required. The signal from the data processor to the scanning device can include one or more items of data such as, but not limited to, information relating the start and/or termination of a data stream to the data processor, retransmission of data, instructions on the type and/or location of the scan of the patient, duration of the scan of the patient, and the like.

A data terminal 60 is connected to the data processor. The data terminal is designed to provide information to a technician, doctor and/or others about the progress of the scan, the data for the prosthetic implant, the data generated for the prosthetic implant and/or other types of information. In one typical arrangement, the data terminal includes a screen that provides a multi-dimensional view of the prosthetic implant to be formed. The data terminal can be alternatively or additionally be used to input information to the data processor. Such input information can include, but is not limited to, date and time information, patient information, medical personnel information, medical facility information, instrumentation information, input for the scanning device, output from one or more scanning devices, software and/or hardware selection for data processing by the data processor, database selection for the data processor, data modifications to the data from the one or more scanning devices, data modification of data generated by the data processor, molding process information, prosthetic implant materials, prosthetic implant structures, and/or the like.

Once data processor 50 has generated the information for the production of the prosthetic implant, at least a portion of the information is transmitted to molding machine 70. As illustrated in FIG. 1, the data from the data processor is transmitted to the molding machine via wire or cable 52. As can be appreciated, a portion or all of the data from the data processor can be manually inputted into the molding machine. Furthermore, the data can be filly or partially transmitted to the molding machine by radio waves, microwaves and the like. As shown in FIG. 1, the molding machine is designed to send information to the data processor; however, such communication is not required. The signal from the molding machine to the data processor can include one or more items of data such as, but not limited to, information relating the start and/or termination of a data stream to the molding machine, retransmission of data, molding progress, and the like.

Molding machine 70 is designed to mold and/or extrude a moldable compound from compound receptacle 80 and form a prosthetic implant. The data that is generated by the data id processor is used to manually and/or automatically modify one or more mold settings, modify the shape of a molding cavity, and/or modify an extruder opening. Once the modifications have been made, a moldable compound is directed into one or more molding cavities and/or through one or more extruders to at least partially form the prosthetic implant. The one or more types of moldable compound to be used to form the prosthetic implant can be selected automatically or manually selected. Typically, the moldable compound type(s) is selected by the data processor based upon predefined criteria for the prosthetic implant or by medical personnel via data terminal 60. Generally the moldable compound is in a liquid form or in a soft malleable form so that the moldable compound can be easily formed in a mold and/or extruded. The moldable compound is also formulated such that the moldable compound can be at least partially hardened after being formed so that the formed prosthetic implant will retain its shape and size after being implanted into the patient. One or more additives can be incorporated into the prosthetic implant during the molding process via additive receptacle 90. The one or more types of additives to be included in the prosthetic implant can be selected automatically or manually. Typically, the additive (s) is selected by the data processor based upon predefined criteria for the prosthetic implant or by medical personnel via data terminal 60. Generally these additives include bone and/or tissue growth promoters; however, other types of additives can be used.

Figure 3:
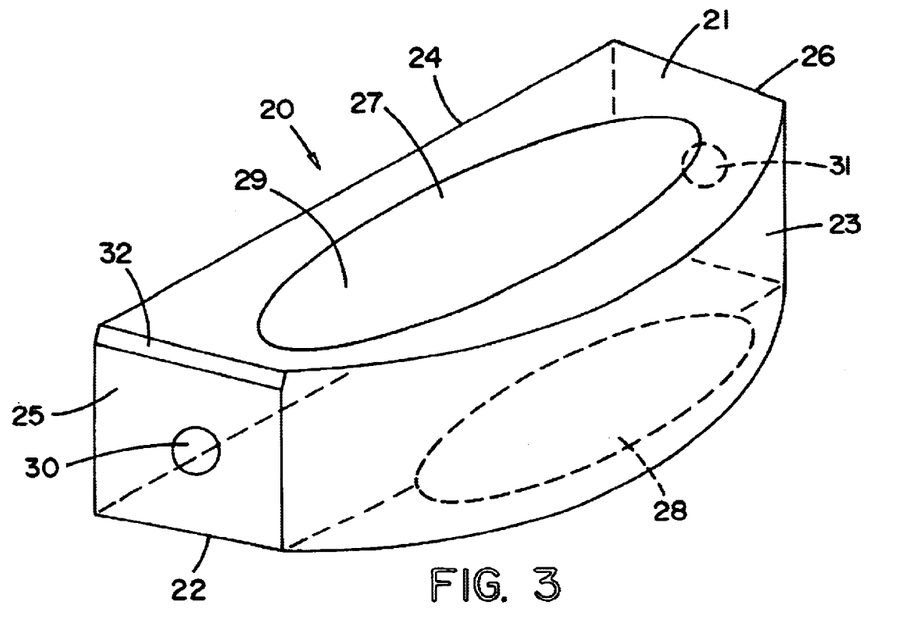
FIG. 3 is an enlarged perspective view of one type of prosthetic implant that can be produced by the present invention.

The prosthetic implant formed by the molding machine may be totally formed by the moldable compound and additives, if use, or can also include one or frame and/or secondary structures. Referring to FIG. 3, prosthetic implant 20 is substantially formed from a mold in the molding machine using the moldable compound.

The particular prosthetic implant illustrated in FIG. 3 is designed to be inserted in an intervertebral disk space between two vertebrae of the spinal column. The prosthetic implant is illustrated as a cage-like structure having a top wall 21, a bottom wall 22, a front wall 23, a back wall 24, a first end wall 25, and a second end wall 26. The top wall and bottom wall are designed to engage with the underside surface of the vertebrae. The top and bottom walls also include openings 27, 28, respectively. The openings are illustrated as semi-oval shaped; however, other shapes can be used. The size of the opening is selected so that materials can be inserted into the openings such as, but not limited to, bone, tissue, cells, medicine, etc. The prosthetic implant also includes a cavity 29. Cavity 29 is shown to be in communication with openings 27, 28. The cavity is designed to increase the amount of packing material that can be inserted in the prosthetic implant. Front wall 23 has an arcuate or curvilinear shape along the longitudinal length of the wall. The arcuate shape of the wall is selected to more closely anatomically match the intervertebral disk space. As can be appreciated, the front wall can have other shapes. Back wall 24 as has a substantially straight or planar face. When the prosthetic implant is positioned in the intervertebral disk space, back wall is positioned closely adjacent to the spinal cord and front wall is positioned adjacent the outer edge of the vertebrae. The curvilinear front wall and the substantially planar or straight back wall are designed to more closely match the intervertebral disk space and to increase the surface area of contact with the vertebrae to assist in reducing slippage and to increase the success rate of the fusion between two vertebrae. The shape of the arcuate surface of front wall is customized to improve the success of inserting the prosthetic implant in the patient. In addition, the shape of the surface of back wall is also customized to improve the success of inserting the prosthetic implant in the patient. First end wall 25 and second end wall 26 include openings 30, 31, respectively. The openings communicate with inner cavity 29. Openings 30, 31 are designed to receiving packing material and to allow for blood flow between the packing material within the cavity and the surrounding regions of the vertebrae. Openings 30, 31 are illustrated as circular; however, other shapes can be used. Openings 30, 31 can alternatively or additionally function as an instrument opening designed to receive an instrument to enable the prosthetic implant to be inserted in the intervertebral disk space in number of different approaches (e.g., anterior, posterior, lateral, and/or lateralscopic approach). The openings can be threaded to receive a threaded instrument. The openings can also be used to secure pedicle screws to the prosthetic implant so as to facilitate attachment to a rod or plate stabilization system to the prosthetic implant. The peripheral edges of some walls of the prosthetic implant are smoothed, rounded off or contoured 32. The rounded off edges minimize or eliminate sharp edges on the prosthetic implant to reduce and/or eliminate pinching of the nerves, and to facilitate in the positioning of the prosthetic implant in the intervertebral disk space.

Figure 4:
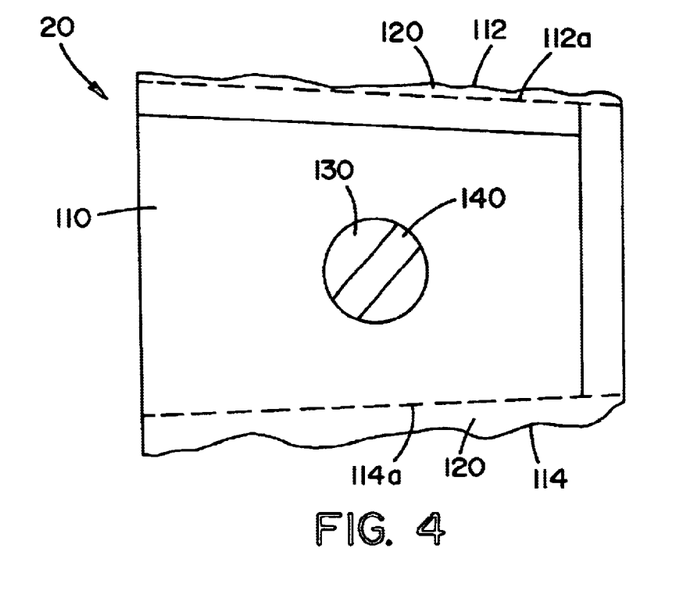
FIG. 4 is an enlarged end of a prosthetic implant showing a moldable compound coated onto the surface of a standard sized prosthetic implant.

Referring now to FIG. 4, a modified prosthetic implant for intervertebral disk space is disclosed. The prosthetic implant is formed by using a preexisting frame or structure. The preexisting frame or structure can be a standard sized and shaped prosthetic implant for intervertebral disk space. This standard sized and shaped prosthetic implant is inserted into the molding machine and the moldable compound is at least partially formed about the standard sized and shaped prosthetic implant to form a custom-sized prosthetic implant. FIG. 4 illustrates the first end 110 of a prosthetic implant similar to the prosthetic implant shown in FIG. 3. The top wall 112 and bottom wall 114 have been custom shaped by use of a moldable compound layer 120. The dashed lines 112a, 114a illustrate the profile of the top and bottom wall, respectively, of the standard sized and shaped prosthetic implant prior to the moldable compound being applied to such walls. The remaining walls of the standard sized and shaped prosthetic implant are shown to have not been coated with the moldable compound; however, such walls can be modified by use of the moldable compound. The profile of the top and bottom wall formed by the moldable compound is selected to closely correspond with the shape and size of the intervertebral disk space the prosthetic implant is to be inserted. FIG. 4 also illustrates that the moldable compound layer 120 on the top wall has a different thickness than on the bottom wall. The thickness, as with the profile, of the moldable compound layer is selected to closely correspond with the shape and size of the intervertebral disk space. FIG. 4 also illustrates the prosthetic implant including a secondary structure in opening 130. The secondary structure is a metal slot that is inserted into the mold of the molding machine so as to be incorporated into the prosthetic implant. The metal slot is designed to receive an insertion instrument and/or function as a connector for a rod or other structure to be connected to the prosthetic implant. As can be appreciated, the slot can be made of material other than metal. Furthermore, the slot configuration can be formed by the mold using the moldable compound.

Figure 5:
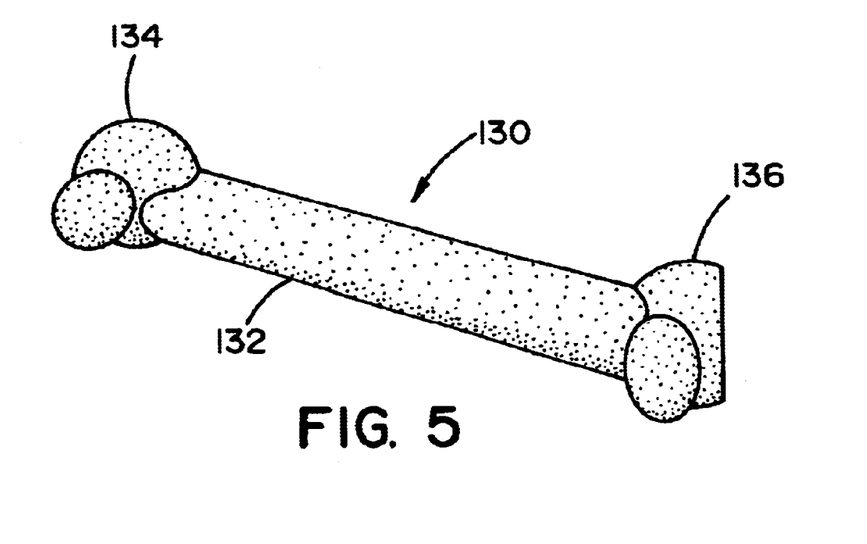
FIG. 5 is a perspective view of a prosthetic implant substantially form by a moldable compound; and, FIG. 6 is a perspective view of a modified prosthetic as shown in FIG. 5.

Referring now to FIG. 5, another prosthetic implant is illustrated. The prosthetic implant 130 has a shape that is very similar to the humerus bone of a human. The prosthetic implant has a generally cylindrical body central body 132 and two end joints 134, 136 that have a partially spherical shape. End joint 136 is shown to be only partially formed. The surface of the prosthetic implant is shown to be slightly rough so as to emulate an actual humerus bone. As can be appreciated, the surface of the prosthetic implant can be made smooth, include one or more internal passageways and/or cavities, and/or include one or more surface openings.

Figure 6:
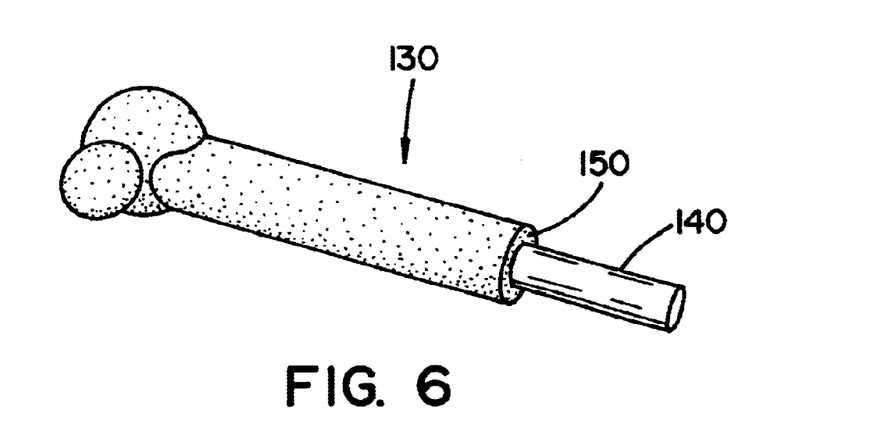

Referring now to FIG. 6, the prosthetic implant represents at least three other embodiments of the invention. In one embodiment, the prosthetic implant in FIG. 6 illustrates a modification to the prosthetic implant of FIG. 5. In this embodiment, FIG. 6, illustrates a partial view of the prosthetic implant of FIG. 5 to reveal that the prosthetic implant is form by use of a structural device 140 in the form of a rod and a moldable compound 150 formed about the rod. In this embodiment, the humerus bone is formed by placing a certain sized and shaped rod into the molding machine. Thereafter, a molding compound is formed about the rod to form a substantially complete humerus bone as shown in FIG. 5. The rod provides strength and structural rigidity to the prosthetic implant. In another embodiment represented by FIG. 6, the prosthetic implant includes a secondary structure extending from a portion of the prosthetic implant. In this embodiment, FIG. 6 represents a prosthetic implant that is a partial humerus bone. Such a prosthetic implant is used to repair only a portion of the original humerus bone. The rod 140 is used as a connector to attach the prosthetic implant to the existing humerus bone. The rod only partially extends into the moldable compound. In still another represented by FIG. 6, the prosthetic implant includes a secondary structure extending from a portion of the prosthetic implant and a structural device that extends substantially the complete longitudinal length into the moldable compound. In this embodiment, the rod is both a secondary structure for attaching the prosthetic implant to another bone and a structural device upon which the moldable compound is formed.

After the molding machine has formed the prosthetic implant, the prosthetic implant is sent to a mold finisher 100. The mold finisher can be a manual workstation and/or an automated device. At the mold finisher, the prosthetic implant is inspected, cleaned, disinfected, sanitized, sterilized, smoothed, roughened, etched, hardened, cut, coated, packed with materials, labeled, and/or packaged. When the mold finisher includes one or more automated functions, data can be sent between the data processor and mold finisher. This data can be used to confirm that the desired shaped and sized prosthetic implant was produced, to suggest and/or make shape and/or size changes to the prosthetic implant, etc. Once the prosthetic implant has been processed in the mold finisher, the prosthetic implant can be surgically implant in the patient and/or stored for later implantation.

Figure 2:
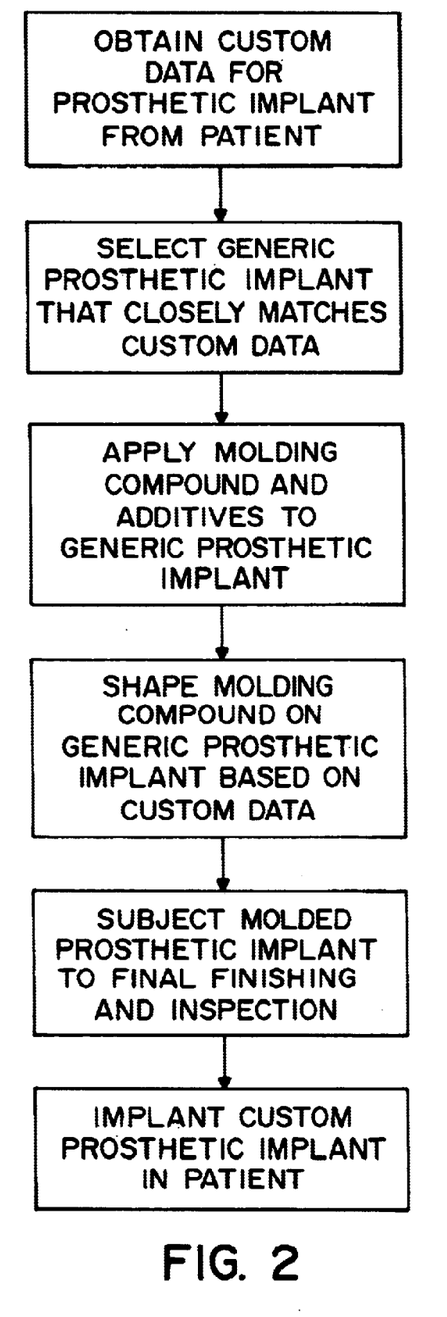
FIG. 2 is a flow chart illustrating a process for producing a custom-sized prosthetic implant of the present invention.

Referring now to FIG. 2, a flow chart illustrates one method for producing the custom-sized prosthetic implant in accordance with the present invention as illustrated in FIGS. 4 and 6. As illustrated in FIG. 2, data is first acquired for the prosthetic implant. Once the data is acquired, a standard prosthetic implant having a close shape and size to the acquired data is selected. This standard prosthetic implant is inserted into the molding machine wherein a molding material is at least partially coated onto the surface of the standard prosthetic implant. The molding material is shaped on the surface of the standard prosthetic implant until the shape and size of the prosthetic implant is customized to the acquired data. After the moldable compound is applied and shaped on the surface of the standard prosthetic implant, the custom-sized prosthetic implant is finished and inspected to determine if any modifications need to be made to the prosthetic implant. After the prosthetic implant has been inspected and finished, the prosthetic implant is implanted into the patient.

It is contemplated that by using this method of production, a custom-sized prosthetic implant can be produced for emergency medical procedures and can be used in outpatient facilities wherein the prosthetic implant is produced and implanted in less than 24 hours. As can be appreciated, the time period for obtaining information for the prosthetic implant, producing the prosthetic implant and surgically implanting the prosthetic implant can encompass more than 24 hours. In medical emergencies or at outpatient facilities, the information for the prosthetic implant can be rapidly obtained by used of various electronic devices such as an MRI, X-ray, etc. The electronic device, at the time of scanning or after the scanning procedure, transmits the acquired data to a data processor that can quickly generate the data needed by a mold machine to form the custom-sized prosthetic implant. Once the data has been generated by the processor, the data can be immediately sent to the molding machine, or reviewed and/or modified by one or more medical personnel prior to being sent to the molding machine. Upon receipt of data, the molding machine forms the prosthetic implant using the selected molding material, selected frames or structures, selected secondary devices, and/or any selected additives. After the molding machine produces the prosthetic implant, a scanner and/or medical personnel inspect the prosthetic implant and make and/or cause to be made any need changes to the prosthetic implant. Once the size and shape of the prosthetic implant is approved, the prosthetic implant can be packed and/or coated with materials prior to being implanted into the patient. By use of this automated procedure, it is conceivable that the custom prosthetic implant could be produced in a few hours or less after the patient has been scanned.

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

I claim:

1. A method for producing a custom prosthetic implant for insertion into a patient comprising:
   a. obtaining information about the site of implant for the prosthetic implant;
   b. processing said obtained information to generate information on the size and shape of the prosthetic implant; and,
   c. transferring at least a portion of the generated information to a molding machine to at least partially form said custom prosthetic implant from a moldable compound, said molding machine including at least one mold cavity that can be varied in size and/or shape, said size and/or shape of said mold cavity altered based at least partially on said data transferred to said molding machine.

2. The method as defined in claim 1, wherein said step of obtaining information is at least partially by the use of at least one electronic scanner, said electronic scanner including a scanner selected from the group consisting of an MRI, ultrasonic device, x-ray machine, a camera, a scope and combinations thereof.

3. The method as defined in claim 1, wherein said step of processing said obtained information includes the use of at least one data processor.

4. The method as defined in claim 3, wherein said at least one data processor generates data to form a multi-dimensional representation of said prosthetic implant.

5. The method as defined in claim 4, including the step of manually modifying said generated data.

6. The method as defined in claim 3, wherein said at least one data processor generates at least one graphical representation of said prosthetic implant.

7. The method as defined in claim 1, wherein said step of transferring at least a portion oft he generated information to a molding machine includes a transmission device selected from the group consisting of wires, cables, electromagnetic waves, and combinations thereof.

8. The method as defined in claim 1, including the steps of flowing said moldable compound into at least one mold cavity and at least partially forming said prosthetic implant in said mold cavity and subsequently hardening at least a portion of said moldable compound.

9. The method as defined in claim 1, wherein said moldable compound is at least partially hardened by exposure to heat, radiation, catalysts, chemical reactants, electromagnetic waves, sound waves, and combinations thereof.

10. The method as defined in claim 1, wherein said moldable compound includes a material selected from the group consisting of bone, cartilage, calcium-phosphate compounds, ceramics, metals, polymers, co-polymers, resins, thermoplastics, and mixtures thereof.

11. The method as defined in claim 1, including the step of flowing multiple types of said moldable compounds into said at least one mold cavity.

12. The method as defined in claim 1, including the step of mixing at least one biological additive with said moldable compound with at least one of said moldable compounds prior to fully molding said moldable compound in said mold cavity.

13. The method as defined in claim 1, including the step of at least partially coating a surface of said prosthetic implant with a substance selected from the group consisting of a biological additive, cells, and combinations thereof.

14. The method as defined in claim 1, including the step of including readable information pertaining to said prosthetic implant on said prosthetic implant, said readable information including information selected from the group consisting of types of moldable material, size and shape information used to form the prosthetic implant, internal features of said prosthetic implant, type of additives included on and/or in said prosthetic implant, and combinations thereof.

15. The method as defined in claim 1, wherein said molding machine can form multiple types of prosthetic implants as well as multiple shaped and sized prosthetic implants for each of the types of said prosthetic implants.

16. The method as defined in claim 1, including the step of inserting at least one structural component in said molding cavity and at least partially coating said structural component with said moldable compound.

17. The method as defined in claim 1, including the step of selecting the shape and/or size of said structural component based at least partially on said obtained information.

18. The method as defined in claim 1, including the step of inserting at least one secondary component in said molding cavity and at least partially coating said structural component with said moldable compound.

19. The method as defined in claim 1, including the step of modifying at least a portion of said prosthetic implant after said prosthetic implant has been removed from said molding machine, said step including a step selected from the group consisting of labeling, cutting, smoothing, disinfecting, etching, and combinations thereof.

20. A method for producing a custom prosthetic implant for insertion into a patient comprising:
  a. scanning a patient to obtain information about the site of implant for the custom prosthetic implant, said scanning including an MRI, an ultrasonic device, an x-ray machine, a camera, a scope, and combinations thereof;
  b. processing said obtained information by the use of at least one data processor to generate information for a computer generated custom prosthetic implant having a particular multi-dimensional size and shape for insertion into the site of the implant;
  c. transferring at least a portion of the generated information to a forming machine for use in at least partially forming a custom prosthetic implant from a moldable compound;
  d. flowing said moldable compound having a generally soft putty property into at least one mold cavity to at least partially form said custom prosthetic implant in said mold cavity; and,
  e. finalizing the shape of said formed custom prosthetic implant to obtain a size and shape that substantially matches the size and shape of said computer generated prosthetic implant, said finalizing step including scanning said formed custom prosthetic implant subsequently modifying the shape and size of the custom prosthetic implant by a process which includes laser cutting, smoothing, minor sizing, etching, and combinations thereof.

21. The method as defined in claim 20, wherein said at least one data processor generates at least one graphical representation of said prosthetic implant.

22. The method as defined in claim 20, including the step of manually modifying said generated data.

23. The method as defined in claim 20, wherein said moldable compound substantially forms the complete custom prosthetic implant in said mold cavity.

24. The method as defined in claim 20, wherein said moldable compound is formed about a preexisting structure to form the complete custom prosthetic implant in said mold cavity.

25. The method as defined in claim 20, including the step of hardening at least a portion of said moldable compound.

26. The method as defined in claim 20, wherein said moldable compound includes a material selected from the group consisting of bone, cartilage, calcium-phosphate compounds, ceramics, metals, polymers, co-polymers, resins, thermoplastics, and mixtures thereof.

27. The method as defined in claim 20, including the step of mixing of at least one biological additive with said moldable compound.

28. The method as defined in claim 20, including the step of at least partially coating a surface of said prosthetic implant with a substance selected from the group consisting of a biological additive, cells, and combinations thereof.

29. The method as defined in claim 20, including the step of including readable information pertaining to said prosthetic implant on said prosthetic implant, said readable information including information selected from the group consisting of types of moldable material, size and shape information used to form the prosthetic implant, internal features of said prosthetic implant, type of additives included on and/or in said prosthetic implant, and combinations thereof.

* * * * *